(12) United States Patent
Chakra et al.

(10) Patent No.: US 8,346,532 B2
(45) Date of Patent: Jan. 1, 2013

(54) MANAGING THE CREATION, DETECTION, AND MAINTENANCE OF SENSITIVE INFORMATION

(75) Inventors: Al Chakra, Apex, NC (US); John K. Gerken, III, Raleigh, NC (US); Roderick C. Henderson, Apex, NC (US); Ruthie D. Lyle, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 615 days.

(21) Appl. No.: 12/171,666

(22) Filed: Jul. 11, 2008

(65) Prior Publication Data

US 2010/0011000 A1  Jan. 14, 2010

(51) Int. Cl.
*G06F 17/30* (2006.01)
(52) U.S. Cl. ............................................. 704/1; 726/28
(58) Field of Classification Search .......... 707/738–740, 707/757
See application file for complete search history.

(56) References Cited

U.S. PATENT DOCUMENTS

| | | | | |
|---|---|---|---|---|
| 6,553,365 | B1* | 4/2003 | Summerlin et al. | 707/740 |
| 2003/0028631 | A1* | 2/2003 | Rhodes | 709/224 |
| 2003/0120949 | A1* | 6/2003 | Redlich et al. | 713/200 |
| 2004/0193910 | A1* | 9/2004 | Moles | 713/200 |
| 2005/0182765 | A1* | 8/2005 | Liddy | 707/5 |
| 2006/0005247 | A1* | 1/2006 | Zhang et al. | 726/26 |
| 2006/0075228 | A1* | 4/2006 | Black et al. | 713/167 |
| 2006/0089857 | A1* | 4/2006 | Zimmerman et al. | 705/2 |
| 2007/0294199 | A1* | 12/2007 | Nelken et al. | 706/50 |
| 2008/0046757 | A1* | 2/2008 | Staddon et al. | 713/189 |
| 2008/0097946 | A1* | 4/2008 | Oliver et al. | 706/46 |
| 2008/0162652 | A1* | 7/2008 | True et al. | 709/206 |
| 2009/0158441 | A1* | 6/2009 | Mohler et al. | 726/27 |
| 2009/0192979 | A1* | 7/2009 | Lunde | 707/1 |
| 2009/0198654 | A1* | 8/2009 | Surendran et al. | 707/3 |
| 2009/0208142 | A1* | 8/2009 | Treadwell et al. | 382/321 |
| 2010/0122178 | A1* | 5/2010 | Konig et al. | 715/738 |

\* cited by examiner

*Primary Examiner* — James Trujillo
*Assistant Examiner* — Dawaune Conyers
(74) *Attorney, Agent, or Firm* — Jose Gutman; Fleit Gibbons Gutman Bongini & Bianco PL

(57) ABSTRACT

A method, information processing system, and computer program storage product for managing information within an electronic file are provided. A plurality of information sets within an electronic file is analyzed. At least one of the information sets is compared to at least one statistical classification model. The statistical classification model includes one or more probabilities associated with a plurality of analyzed information sets that indicate a likelihood that a respective analyzed information set is classified sensitive information. The at least one information set is determined to substantially match at least one analyzed information set in the statistical classification model. The probability associated with the at least one analyzed information set is determined whether to be above a threshold. The at least one information set is classified as sensitive information in response to determining that the probability is above the threshold.

20 Claims, 10 Drawing Sheets

MANAGING THE CREATION, DETECTION, AND MAINTENANCE OF SENSITIVE INFORMATION

FIELD OF THE INVENTION

The present invention generally relates to the field of information management systems, and more particularly relates to managing sensitive information using statistical analysis.

BACKGROUND OF THE INVENTION

As more and more electronic information is generated by governments and businesses, security and privacy of this information becomes problematic. Governments and business are required to ensure personal information and documents containing classified or confidential information are properly managed. The safeguarding of electronic documents is paramount to ensure that personal information is protected from the threat of identity theft and privacy breaches.

With respect to governments, information needs to be secured while still enforcing the public's right to be informed of the activities of the governments. With respect to businesses, corporate and personal information needs to be secured. For instance, in a web-based medical record use case, there is a need to control a doctor's access levels for viewing the record versus a medical receptionist's access rights. The doctor should be given complete access to his patient's medical history while the medical receptionist should be prevented from viewing a patient's sensitive data.

Most current information management systems are rule-based systems. Rule-based systems are problematic because their learning capabilities are limited. For example, an administrator is required to create the rules used by the system. This is very time consuming and does not allow the system to easily adapt to changing environments. If information does not fall within a rule the information is not protected even though the information is similar to other protected information.

Therefore a need exists to overcome the problems with the prior art as discussed above.

SUMMARY OF THE INVENTION

In one embodiment, a method for managing information within an electronic file is disclosed. The method includes analyzing a plurality of information sets within an electronic file. At least one of the information sets in the plurality of information sets is compared to at least one statistical classification model. The statistical classification model includes one or more probabilities associated with a plurality of analyzed information sets that indicate a likelihood that a respective analyzed information set is classified sensitive information. The at least one information set is determined to substantially match at least one analyzed information set in the statistical classification model. The probability associated with the at least one analyzed information set is determined whether to be above a given threshold. The at least one information set is classified as sensitive information in response to determining that the probability associated with the at least one analyzed information set is above a given threshold.

In another embodiment, an information processing system for managing information within an electronic file is disclosed. The information processing system includes a memory and a processor that is communicatively coupled to the memory. The information processing system also includes an information manager that is communicatively coupled to the memory and the processor. The information manager is adapted to analyze a plurality of information sets within an electronic file. At least one of the information sets in the plurality of information sets is compared to at least one statistical classification model. The statistical classification model includes one or more probabilities associated with a plurality of analyzed information sets that indicate a likelihood that a respective analyzed information set is classified sensitive information. The at least one information set is determined to substantially match at least one analyzed information set in the statistical classification model. The probability associated with the at least one analyzed information set is determined to be above a given threshold. The at least one information set is classified as sensitive information in response to determining that the probability associated with the at least one analyzed information set is above a given threshold.

In yet another embodiment, a computer program storage product for managing information within an electronic file is disclosed. The computer program storage product includes instructions for analyzing a plurality of information sets within an electronic file. At least one of the information sets in the plurality of information sets is compared to at least one statistical classification model. The statistical classification model includes one or more probabilities associated with a plurality of analyzed information sets that indicate a likelihood that a respective analyzed information set is classified sensitive information. The at least one information set is determined to substantially match at least one analyzed information set in the statistical classification model. The probability associated with the at least one analyzed information set is determined to be above a given threshold. The at least one information set is classified as sensitive information in response to determining that the probability associated with the at least one analyzed information set is above a given threshold.

An advantage of the various embodiments of the present invention is that sensitive and private information is maintained in a secure manner. Statistical classification models are created and updated to provide an adaptive mechanism for protecting sensitive information. Users can be notified when sensitive information is being created. Users can also be prevented from accessing sensitive information while still being able to access non-sensitive information within an electronic document.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention.

DETAILED DESCRIPTION

As required, detailed embodiments of the present invention are disclosed herein; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

General Operating Environment

Figure 1:
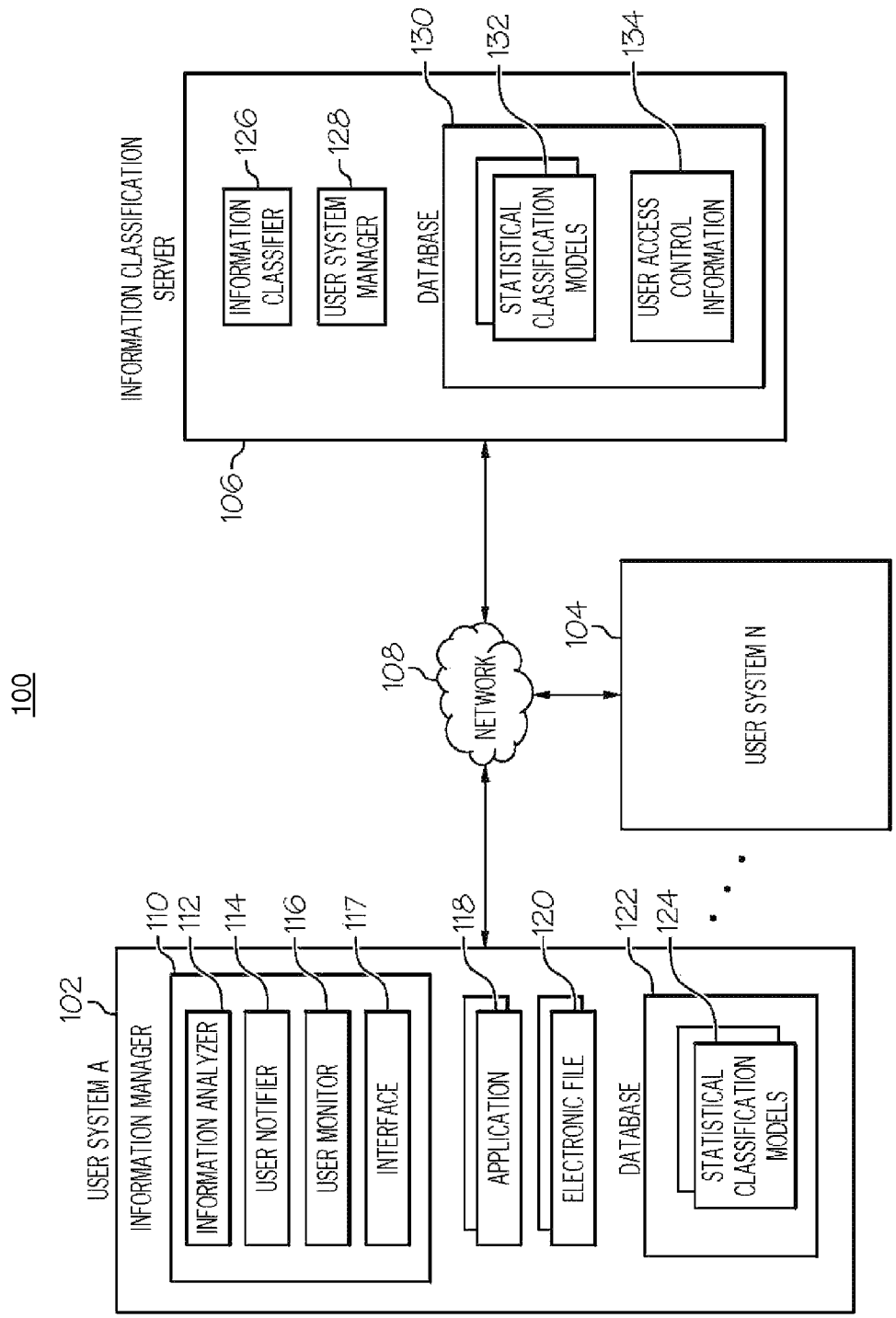
FIG. 1 is block diagram illustrating a general overview of an operating environment according to one embodiment of the present invention.

According to one embodiment of the present invention as shown in FIG. 1 a general overview of an operating environment 100 is illustrated. In particular, the operating environment 100 includes one or more information processing systems 102, 104, 106 communicatively coupled to each other through a network 108. The network 108 can comprise wired and/or wireless technologies. The information processing systems can include one or more user systems 102, 104 and one or more servers such as the information classification server 106. Further, the information processing systems 102, 104, 106 can comprise a desktop computer, notebook computer, workstation, wireless communication device, personal digital assistant, and the like.

Each of the user systems 102, 104, in one embodiment, includes an information manager 110. The information manager 110 includes an information analyzer 112, a user notifier 114, a user monitor 116, and an interface 117. The information analyzer 112 analyzes electronic information that a user is currently interacting to identify sensitive information. The user notifier 114 notifies the user that sensitive information has been identified. The interface 117 allows the information manager 110 to communicate with the information classification sever 106.

The user systems 102, 104 also include one or more applications 118 such as (but not limited to) a web browser, a word processing client, an email client, a spreadsheet client, a media player, and a photo editor. The user systems 102, 104 also include one or more electronic files 120. Electronic files 120 can include any type of electronic information or data. A database 122 can be optionally included on the user systems 102,104 that include local copies of statistical classification models 124 used for classifying electronic information or subsets of electronic information with one or more levels of security. The database 122 is optional, in one embodiment, since information being analyzed can be sent to the information classification server 106 as compared to analyzing the information locally.

The information classification server 106, in one embodiment, includes an information classifier 126, a user system manager 128, and a database 130. The information classifier 126 classifies information as sensitive information and generates statistical classification models 132 based on information that has been classified as sensitive. The user system manager 128 interfaces with each user system to update any local statistical classification models 124 and receive electronic documents comprising newly created sensitive information.

The database 130 includes statistical classification models 132 and user access control information 134. The statistical classification models include statistical information used by the information classifier 126 and the information analyzer 112 for classifying and identifying sensitive information. The user access control information 134 is utilized by the user monitor 116 to determine whether or not a particular user has access rights to interact with sensitive information.

The user systems 102, 104, the information classification server 106, and their respective components are discussed in greater detail below. It should also be noted that one or more of the components of the information processing systems 102, 104, 106 can be distributed across multiple systems as compared to residing on a single system as shown in FIG. 1.

Information Processing System

Figure 2:
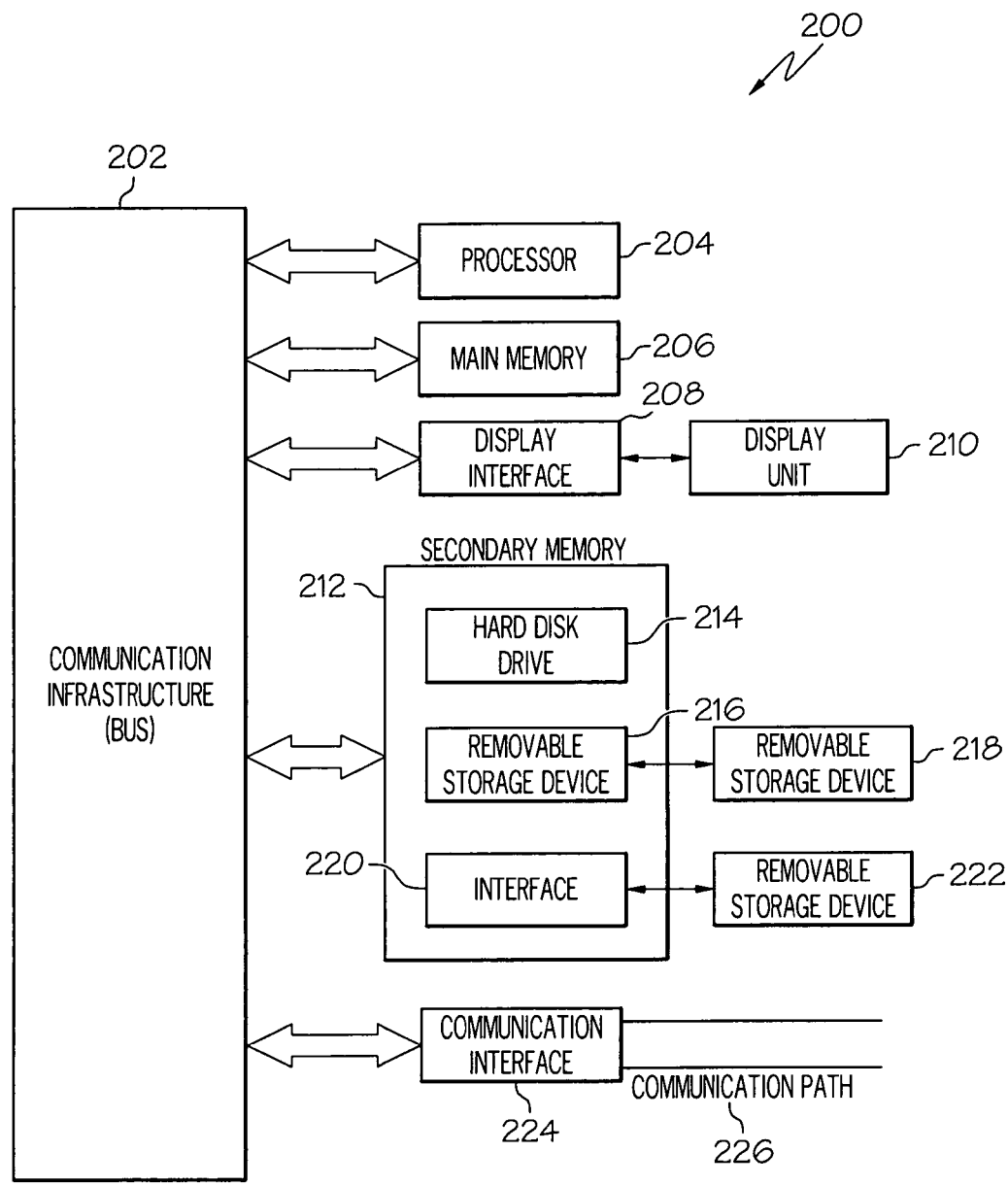
FIG. 2 is a block diagram illustrating a detailed view of an information processing system according to one embodiment of the present invention.

FIG. 2 is a high level block diagram illustrating a more detailed view of a computing system 200 such as the user system 102 or information classification server 106 useful for implementing either the information manager 110 and/or the information classifier 126 according to one or more embodiments of the present invention. The computing system 200 is based upon a suitably configured processing system adapted to implement an exemplary embodiment of the present invention. For example, a personal computer, workstation, or the like, may be used.

In one embodiment of the present invention, the computing system 200 includes one or more processors, such as processor 204. The processor 204 is connected to a communication infrastructure 202 (e.g., a communications bus, crossover bar, or network). Various software embodiments are described in terms of this exemplary computer system. After reading this description, it becomes apparent to a person of ordinary skill in the relevant art(s) how to implement the invention using other computer systems and/or computer architectures.

The computing system 200 can include a display interface 208 that forwards graphics, text, and other data from the communication infrastructure 202 (or from a frame buffer) for display on the display unit 210. The computing system 200 also includes a main memory 206, preferably random access memory (RAM), and may also include a secondary memory 212 as well as various caches and auxiliary memory as are normally found in computer systems. The secondary memory 212 may include, for example, a hard disk drive 214 and/or a removable storage drive 216, representing a floppy disk drive, a magnetic tape drive, an optical disk drive, and the like. The removable storage drive 216 reads from and/or writes to a removable storage unit 218 in a manner well known to those having ordinary skill in the art.

Removable storage unit 218, represents a floppy disk, a compact disc, magnetic tape, optical disk, etc. which is read by and written to by removable storage drive 216. As are appreciated, the removable storage unit 218 includes a computer readable medium having stored therein computer software and/or data. The computer readable medium may include non-volatile memory, such as ROM, Flash memory, Disk drive memory, CD-ROM, and other permanent storage. Additionally, a computer medium may include, for example, volatile storage such as RAM, buffers, cache memory, and network circuits. Furthermore, the computer readable medium may comprise computer readable information in a transitory state medium such as a network link and/or a network interface, including a wired network or a wireless network that allow a computer to read such computer-readable information.

In alternative embodiments, the secondary memory 212 may include other similar means for allowing computer programs or other instructions to be loaded into the computing system 200. Such means may include, for example, a removable storage unit 222 and an interface 220. Examples of such may include a program cartridge and cartridge interface (such as that found in video game devices), a removable memory chip (such as an EPROM, or PROM) and associated socket, and other removable storage units 222 and interfaces 220 which allow software and data to be transferred from the removable storage unit 222 to the computing system 200.

The computing system 200, in this example, includes a communications interface 224 that acts as an input and output and allows software and data to be transferred between the computing system 200 and external devices or access points via a communications path 226. Examples of communications interface 224 may include a modem, a network interface (such as an Ethernet card), a communications port, a PCM-CIA slot and card, etc. Software and data transferred via communications interface 224 are in the form of signals which may be, for example, electronic, electromagnetic, optical, or other signals capable of being received by communications interface 224. The signals are provided to communications interface 224 via a communications path (i.e., channel) 226. The channel 226 carries signals and may be implemented using wire or cable, fiber optics, a phone line, a cellular phone link, an RF link, and/or other communications channels.

In this document, the terms "computer program medium," "computer usable medium," "computer readable medium", "computer readable storage product", and "computer program storage product" are used to generally refer to media such as main memory 206 and secondary memory 212, removable storage drive 216, and a hard disk installed in hard disk drive 214. The computer program products are means for providing software to the computer system. The computer readable medium allows the computer system to read data, instructions, messages or message packets, and other computer readable information from the computer readable medium.

Computer programs (also called computer control logic) are stored in main memory 206 and/or secondary memory 212. Computer programs may also be received via communications interface 224. Such computer programs, when executed, enable the computer system to perform the features of the various embodiments of the present invention as discussed herein. In particular, the computer programs, when executed, enable the processor 204 to perform the features of the computer system.

Securing Sensitive Information Using Statistical Classification

As discussed above, the various embodiments of the present invention secure sensitive information and maintain the privacy of this information utilizing one or more statistical models. The following is a more detailed discussion illustrating various embodiments that manage the creating, deletion, and maintenance of sensitive information. Sensitive information can be any information that has been designated by a government, business, individual, or the like as needing to be secured or kept private.

In particular, the information classifier 126 generates, maintains, and updates statistical classification models 132 that are used by the information analyzer 112 to determine whether content within an electronic file 120 is sensitive information. An electronic file 120 can be, but is not limited to, an electronic document, an email, an image file, an audio file, a video file, and the like. An entire electronic file 120 can be sensitive or only subsets of information within the electronic document may be sensitive.

The statistical classification models 132 are initially created by training the information classifier 126. The information classifier 126 is a learning engine that continually updates the statistical classification models 132 based on information received from users, administrators, and automated agents. The training process can include an administrator populating the information classifier 126 with multiple electronic files 120 comprising information tagged as "sensitive", "classified", "private", or the like. It should be noted that the term "sensitive information" from hereon in is used to refer to any information that is designated as sensitive, classified, private, and/or the like. Sensitive information can be any information designated by law, a business, a government, or an individual as having limited accessibility. Stated differently, sensitive information is privileged and/or proprietary information.

The information classifier 126 can also receive electronic files 120 from users that have tagged information as sensitive. For example, a user via the application 118 can generate an email with information that the user has tagged as sensitive. The information manager 110 via the interface 117 then transmits this email (e.g. electronic file 120) to the information classifier 126. The information classifier 126 analyzes the electronic information received from the administrators and users to identify sensitive information. For example, information within an electronic file 120 that has been designated as sensitive is associated with metadata indicating the sensitive nature of the information.

The information classifier 126, in one embodiment, analyzes the electronic files 120 in various contexts. For example, the information classifier 126 analyzes an electronic file 120 as a whole and/or by each page, paragraph, line, sentence, phrase in each sentence, and/or word. The sensitive information and non-sensitive information in each of these different contexts are recorded by the information classifier 126. This allows the information classifier 126 to generate (and update) the statistical classification models 132. The information classifier 126 can record multiple dimensions and parameters associated with information designated as sensitive and/or non-sensitive to determine different contexts when information is sensitive and at what level of sensitivity.

For example, after the above training process, the information classifier 126 has determined that the information set "the quick brown fox" is classified as sensitive information 90% of the time when used in the following complete sentence "the quick brown fox jumps over the lazy dog". In this example, the information classifier 126 has also determined that the information set "the quick brown fox" is classified as sensitive information 10% of the time when used in a sentence comprising the information set "zoo". Even further, the information classifier 126 has also determined that the word "fox" is classified as sensitive 3% of the time when in a sentence without the information sets "jumps over the lazy dog" and "zoo". These probabilities determined by the information classifier 126 are used to create the statistical models 132 for identifying sensitive and non-sensitive information within an electronic information set. It should be noted that the information classifier 126 continually updates the statistical models 132 as more and more electronic information sets are received. The statistical models 132 become more accurate as the information classifier is able to analyze more electronic information sets.

Additionally, the information classifier 126, in one embodiment, decodes the meaning or idea being conveyed by the sensitive information. For example, the information classifier 126 identifies the features and parts of the sensitive information such as (but not limited to) grammar, semantics, syntax, idioms, and the like in order to determine the meaning/idea of the sensitive information. This allows the information classifier 126 to identify alternate/equivalent forms of the sensitive information. For example, using the information set "the quick brown fox", the information classifier 126 can determine that the information set "the fast brown fox" is an equivalent form of "the quick brown fox". Therefore, the statistical classification model 132 includes this equivalency information as well. In other words, the probability information associated with "the quick brown fox" also applies to its equivalents such as "the fast brown fox" as well.

In another example the information classifier 126 has determined that the information set "the meeting will be held on December 1" has been classified as sensitive information. Therefore, after analyzing this information set, the information classifier 126 determines that one equivalent information set is "we are getting together on the first Tuesday in December". By determining equivalent forms of sensitive information, the information classifier 126 or the information analyzer 112 user system 102 can detect sensitive information even though a user has changed the text or context of the sensitive information.

Each user system 102, 104, as discussed above, includes an information manager 110 that monitors information interaction such as (but not limited to) the creation, deletion, addition, and reviewing of electronic information at the user system 102, 104. The information manager 110 can be a stand alone module or integrated into applications 118 such as (but not limited to) a web browser, a word processing client, an email client, a spreadsheet client, a media player, and a photo editor. The information manager 110 registers with the user system manager 128 at the information classification server 106 in order to exchange sensitive/confidential information metadata. For instance, as clients within the enterprise create new types of sensitive data, new metadata is passed to the classification engine so that the statistical classification models 132 can be continually updated.

As the user interacts with electronic information within an electronic file 120 using one or more of the applications 120, the information manager 110 monitors information being interacted with to determine whether or not the information is of a sensitive nature. For example, the information manager 110 either analyzes the information locally via the information analyzer 112 or passes the electronic information to the information classification server via the interface 117 where the information classifier 126 analyzes the information.

If information analyzer 112 is being used to identify sensitive information, the information classification server 106 sends one or more statistical classification models 132 to the user system 102 where they are stored as local models 124. For example, when the information manager 110 is initialized (e.g., when the user system 102 boots up or when an application 118 is started for interaction with the electronic files 120) the manager 110 requests the statistical classification models 132 from the information classification server 106 via the interface 117. Alternatively, the statistical classification models 132 can be transmitted to the user system 102 as the information classifier 126 at the server 106 creates and updates the models 132 or at any time interval there between.

As the information analyzer 112 analyzes the electronic files 120 (e.g., when the user is creating and/or reviewing the information) the information analyzer 112 performs statistical extrapolation to identify sensitive and confidential information within the electronic file 120. For example, the information analyzer 112, parses an electronic file 120 and places content items from the file 120 such as words, phases, sentences or images (based on state of the art digital water markings) into groups based on quantitative information on one or more characteristics inherent in the items.

The characteristics are based on a training set of previously labeled items such as (but not limited to) word processing, email, and spreadsheet documents that include content that has been classified using a tagging scheme, as discussed above. Formally, the problem can be stated as follows: given training data $\{(x_1, y_1), \ldots, (x_n, y_n)\}$ produce a classifier h: X→Y which maps an object x ∈ x to its classification label y ∈ y. For example, if the problem is identifying sensitive text, then $x_1$ is some representation of text in a document like email and y is either "sensitive text" or "non-sensitive text". As sensitive and non-sensitive information is identified, the information analyzer 112 updates the local statistical classification models 124.

If information analyzer 112 is being used to identify sensitive information, the local models 124 can be updated and transmitted to the server 106. The classifier 126 at the server 106 can then update its models 132 accordingly and then send the updated statistical models 132 to the information managers 110 of other user systems. Alternatively, the information manager 110 at the user system 102 can send the updated local models 124 directly to the information managers 110 of other user systems. If the information classifier 126 at the server 106 is being used to identify sensitive information, the classifier 126 can update the models 132 as discussed above and then transmit the updated information to the information managers 110 accordingly.

In one embodiment, the classification engine 126 is based on an application of the Naive Bayes statistical method. The classification engine 126, in this embodiment, uses the Bayes methodology for computing the conditional probability that a given word sequence ("WS") belongs to a classification subject area ("CSA"). There will be several classification subject areas. Therefore, determining the area a word sequence is most associated with involves calculating the probability the word sequence WS belongs to classification subject area $CSA_j$ which is written as $P(CSA_j|WS)$. Based on Bayes' theorem $P(CSA_j|WS)$ is resolved by computing:

$$P(CSA_j|WS)=(P(WS|CSA_j)*P(CSA_j))/P(WS) \qquad \text{EQ (1)}$$

$P(WS|CSA_j)$ is the probability a word sequence appears in a particular $CSA_j$. $P(WS)$ is the probability of a specific word sequence occurring in a document. $P(CSA_j)$ is the probability of a word sequence being in classification subject area $CSA_j$. $P(CSA_j)$ is estimated from the number of word sequences in the training set belonging to $CSA_j$. Each word sequence WS is statistically independent; therefore, EQ 1 can be rewritten as follows:

$$P(CSA_j|WS)=P(WS|CSA_j)*P(CSA_j) \quad \text{EQ (2)}$$

$P(WS|CSA_j)$ is determined by computing the odds of each word sequence in $CSA_j$. Hence EQ 2 becomes:

$$P(CSA_j|WS)=P(WS_0|CSA_j)*P(WS_1|CSA_j)* \ldots \\ *P(WS_{n-1}|CSA_j)*P(CSA_j) \quad \text{EQ (3)}$$

The most probable classification subject area for a given word sequence is represented by the largest value computed in equation 3 for each classification subject area.

As discussed above, the statistical models 132 maintain information that indicates a given probability that information sets are sensitive information. These given probabilities can be determined based on multiple dimensions and parameters, as shown above. Therefore, in one embodiment, various thresholds can be set by administrators of the server 106 that are used by the classifiers to determine when to tag information as sensitive or not sensitive. For example, a threshold of 80% can be set that indicates to the information analyzer 112 or the classifier 126 at the server 106 that if an information set or its equivalent has an 80% or greater probability of being sensitive, then this information set is to be designated as sensitive information. These thresholds can be set at the server 106 and then propagated to the information managers 110 at the user systems 102, 104.

Figure 3:
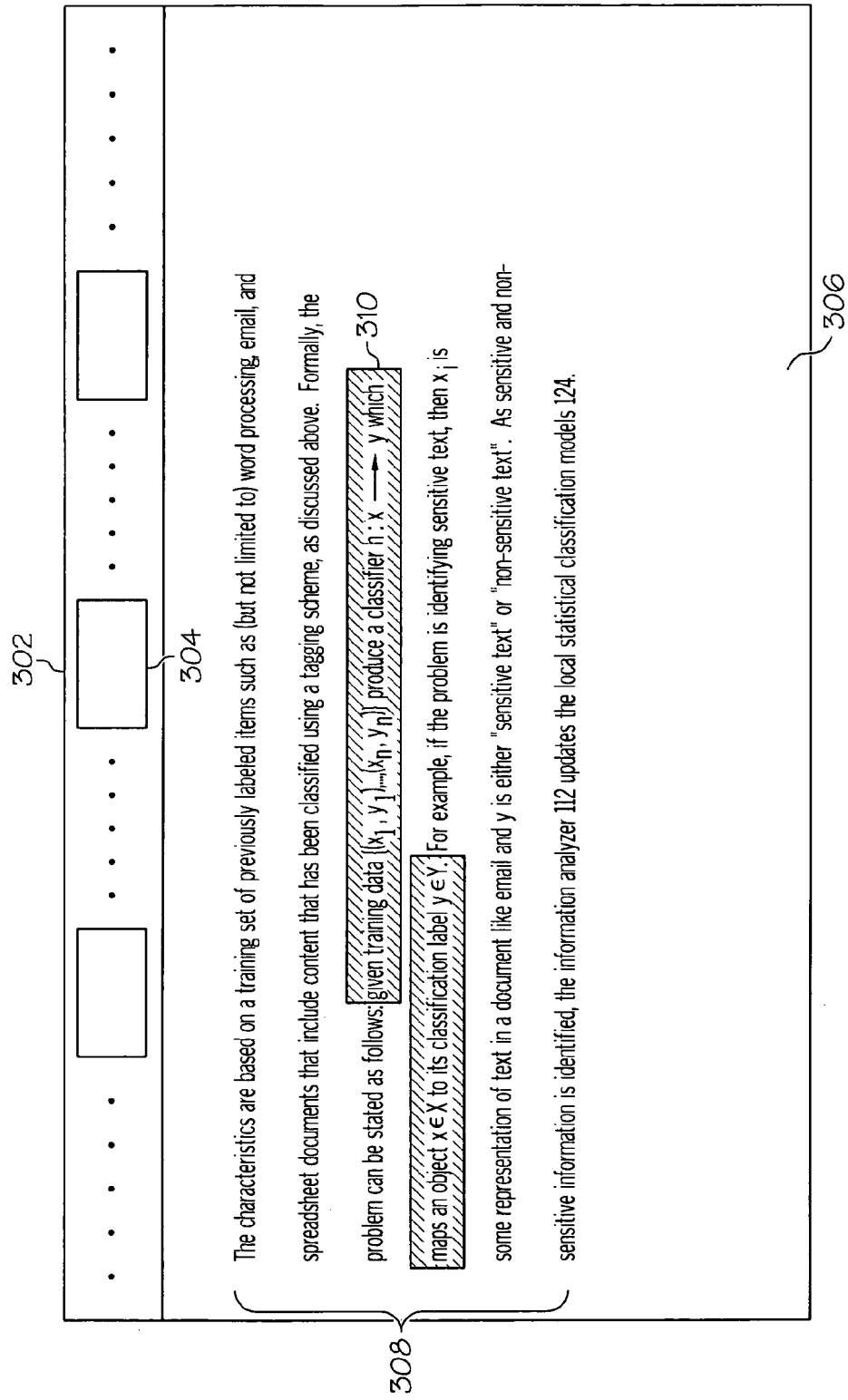
FIG. 3 illustrates sensitive information being visually altered so as to notify a user that sensitive information has been created according to one embodiment of the present invention.

In one embodiment, the information analyzer 112 can analyze the electronic information a user is interacting with in real-time (e.g., as the user is creating the information) to automatically identify sensitive information. In this embodiment, the information analyzer 112 can notify a user via the user notifier 114 that information being created is of a sensitive nature. FIG. 3 shows one example of this embodiment. In particular, FIG. 3 shows a graphical user interface ("GUI") 302 of an application 118 that a user is interacting with to create an electronic file 120. The GUI 302 includes one or more widgets 304 that provide various functions associated with the application 118.

The GUI 302 includes a workspace 306 that displays the information 308 being created by the user. As the user types out the information 308 the information analyzer 112 compares the information being inputted to the local statistical classification models 124. For example, the information analyzer 112 can determine where the information being analyzed falls in a multi-dimensional plot comprising subspaces of information classified as sensitive.

Each subspace can be associated with a different sensitivity level. Also, each subspace can be associated with a probability indicating the likelihood that information within that subspace is sensitive information. If the information analyzer 112 identifies content falling within one or those subspaces and the probability associated with that subspace is above a given threshold, the user can be notified that sensitive information has been created. If the information falls outside of a subspace then the information is identified as non-sensitive information. However, in another embodiment, if the information falls within a given distance to a subspace, then the information can be included as part of that subspace. In this embodiment, if the information is within a given distance that is equal to multiple subspaces, the information is included in the subspace with the higher sensitivity level.

Once the information has been identified as sensitive, the user is notified by the user notifier 114. For example, FIG. 3 shows that the information manager 110 via the user notifier 114 has visually altered an information set 310 to indicate to the user that this information 310 is sensitive information. Although FIG. 3 shows that the sensitive information 310 as being highlighted, the present invention is not limited to such an example. Any type of visual alteration to the information is applicable to the various embodiments of the present invention. The user notifier 114 can also color code different information sets based on their probability of being sensitive information. For example, each color, pattern, shading or other visual appearance change applied to the information sets can be associated with a difference classification probability or a sensitivity level. For example, different sensitivity levels can be assigned to information sets based on the degree of sensitivity associated with the information set.

Once the user is notified that sensitive information has been created, the user can decide to delete the sensitive information or perform another action. For example, the user can assign access rights to the sensitive information. Access rights allow users associated with particular roles to access sensitive information based on their roles. Each role can be associated with an access right, wherein users associated with lower access rights cannot interact with higher levels of sensitive information as users associated with higher access rights.

For example, medical history information may be tagged as sensitive information at a higher level than personal information such as an address. Therefore, a doctor who has a higher access rights than a receptionist is able to view the medical history information while the receptionist is not. Access rights can be based on roles of users such as doctor, CEO, manager, receptionist, and the like. Access rights can also be assigned by an administrator based on various policies setup by the government or business. The access control information associated with sensitive data is stored at the information classification server as shown by the "user access control information" block 134 in FIG. 1. It should be noted that this information can also be continually updated and stored locally on the user systems 102, 104 similar to the statistical classification models 132 discussed above.

If a user does not assign access rights to the sensitive information 310 that has been identified, the information manager 110 can automatically assign rights based on past history as indicated by the local statistical classification models 124 or based on the type of information identified. For example, the information analyzer 112 can also determine the type of information being tagged as sensitive such as medical information, educational, personal, and the like. The information analyzer 112 can analyze the user access control information 134 (which can be stored locally or at the serve 106) to identify user roles that have access rights allowing a user to interact with the identified information type. The information analyzer 112 can then automatically assign user access rights to the sensitive information. The local statistical models 124 can then be updated to reflect this information. By defining access classes or roles for authorizing user access to electronic information at the word, sentence fragment, and/or sentence level the sensitive information is effectively compartmentalized. In other words a user's access to electronic information can be limited at the word, sentence fragment, and/or sentence level.

Also, if the user does not assign access rights to the sensitive information 310, the information manager 110 can prevent the electronic file 120 comprising the sensitive information 310 from being save, printed, or transmitted off of the user system 102. In another embodiment, the information manager 110 is not required to monitor the information being created in real-time. For example, the information manger 110 can initiate the analyzing and identifying processes once a user tries to save, print, or transmit the information off of the user system 102.

In one embodiment, a user can create an electronic file 120 and designate information within that document as sensitive information. The user can also optionally assign access rights to the information he/she as designated as sensitive information. The local statistical models 124 (and the models 132 at the server 106) can then be updated to reflect this information.

In one embodiment, if a user tries to access an electronic file 120 that includes sensitive information such as text or an image on a system without the information manager 110, the file 120 either is not accessible or can be accessed, but with the sensitive information removed or visually altered so as to be incomprehensible. In this embodiment, when an electronic file 120 is stored with sensitive information, the information manager 110 can automatically save this file 120 with the sensitive information removed or visually altered so as to be incomprehensible. Therefore, when the file 120 is open by a system without the information manager 110, the sensitive information is secured and kept private.

In another embodiment the electronic files 120 are stored on a server that is access by user systems as compared to being stored locally. In this embodiment the files 120 are not required to be stored with the sensitive information removed or visually altered. For example, the information classifier 126 at the information classification server 106 can monitor these files and detect when a user system without an information manager 110 is trying to access an electronic file 120 with sensitive information. Once the information classifier 126 detects this, the classifier 126 can remove and/or visually alter the sensitive information so as to be incomprehensible.

Figure 4:
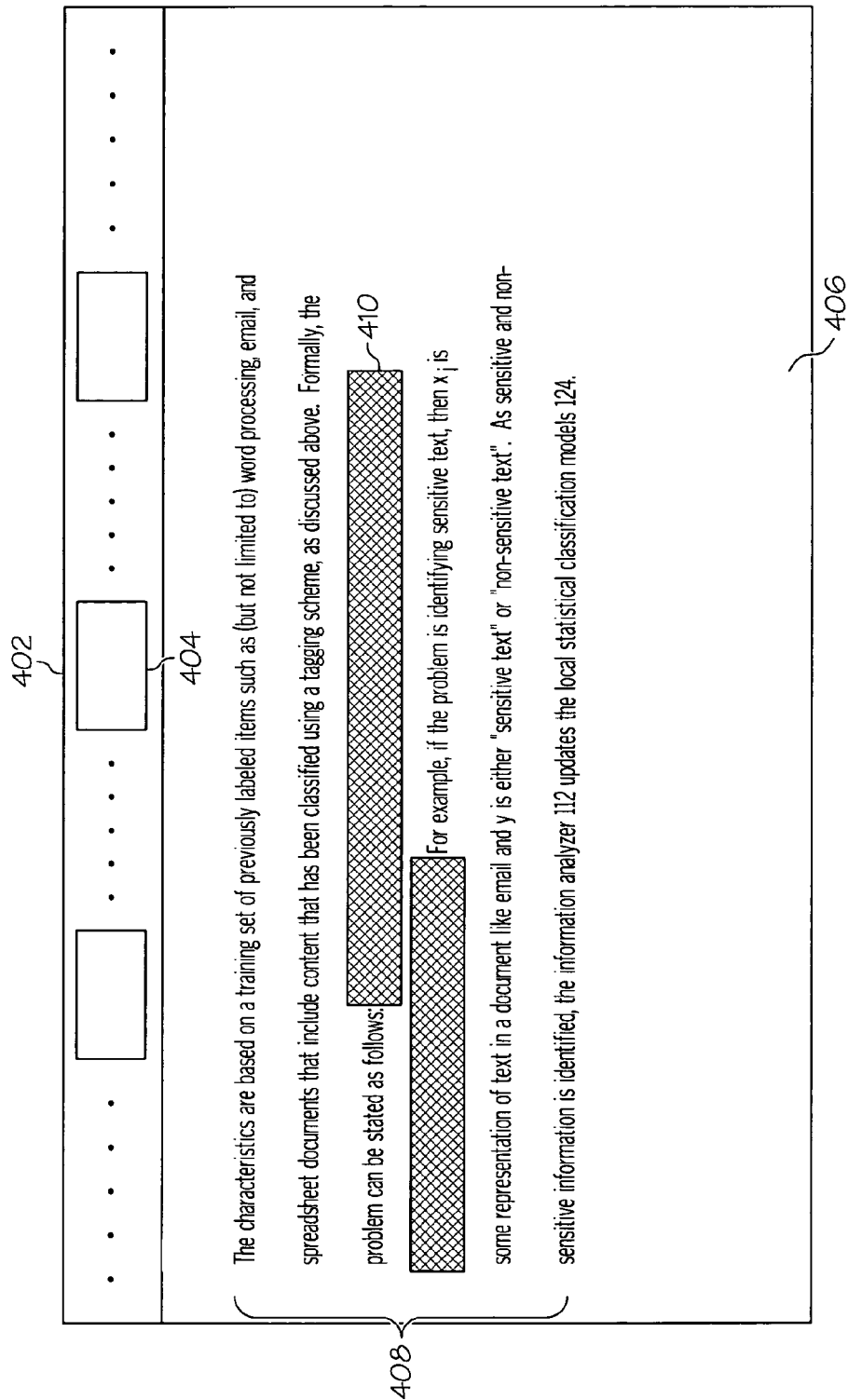
FIG. 4 illustrates sensitive information being visually altered so as to prevent a user from accessing the sensitive information according to one embodiment of the present invention.

FIG. 4 shows one example of preventing unauthorized access to sensitive information. In particular, FIG. 4 shows a GUI 402 of an application 118 that a user is interacting with to review an electronic file 122. The GUI 402 includes one or more widgets 404 that provide various functions associated with the application 118. The GUI 402 includes a workspace 406 that displays the information 408 to the user. In a first example, the user accessing the information 408 is on a system including the information manager 110. In this example, the information manager 110 determines that the user is not associated with the requisite access right for viewing the sensitive information. Therefore, the information manager 110 either removes or visually alters the sensitive information 410. FIG. 4 shows the sensitive information 410 as being redacted.

The information manager 110 can determine the access right associated with the user by identifying the user's role and comparing the user's role to the user access control information 134 to determine the access right associated with the role. The information manager 110 can then analyze the local statistical classification models 124 to determine if the identified access rights matches the access rights associated with the sensitive data. In the example of FIG. 4, the access right associated with the user did not match the rights associated with the sensitive information. Additionally, users access rights can be directly associated with a user as compared to a role. In another example, the user accessing the information 408 is not associated with an information manager 110 so the information has been visually altered to secure the sensitive data.

In addition to electronic files 120 such as (but not limited to) images, documents, and emails, the information manager 110 also dynamically manages access to sensitive web-based information down to the field level and sensitive images. In this embodiment, the information classifier 126 at the server 106 indexes databases and images. The index created is used by the information classifier 126 to generate metadata for the content/information stored in the enterprise database. The metadata, in one embodiment, describes the fields of dynamic protected data; the conditions when the fields are visible, writeable, and required; and the database table and column mapping. The information classifier 126 can identify and tag the database information as sensitive using the statistical models 132 similar to the process discussed above.

The visible condition can be used to determine which authenticated users are allowed access to each field in the database. Thus, an information subset of a web page that contains sensitive and confidential information can be protected. For instance, consider a web-based medical record access system; the information manager 110 controls the level of the record that a doctor can review/modify versus a medical records administrator. Hence, the doctor is given access to his patient's complete medical history while the records administrator is prevented from viewing a patient's sensitive data. This embodiment is similar to the embodiments discussed above where sensitive information is removed or visually altered so that an unauthorized user (e.g., a user on a system without the information manager or without the requisite access rights) cannot interact with sensitive data. In this embodiment, the information manager 110 can dynamically generate code or select that code that hides/encodes the protected sensitive data.

In another embodiment, the information classifier 126 or the information manager 110 is able to declassify information so that it is accessible to everyone. For example, when a user is notified that he/she has created information, the user can declassify the information if the user has the authority to do so. Similarly, an administrator can declassify sensitive information when the information is no longer required to be protected. Also, sensitive information may have metadata associated with it that indicates how long information is to be classified as sensitive. Once the time period has expired, the information manager 110 or the information classifier 126 can automatically declassify the information. Once sensitive information is declassified, the information manager 110 updates the local statistical models 124 and/or the information classifier updates the statistical models 132 accordingly.

An Example of a Process for Creating a Statistical Classification Model

Figure 5:
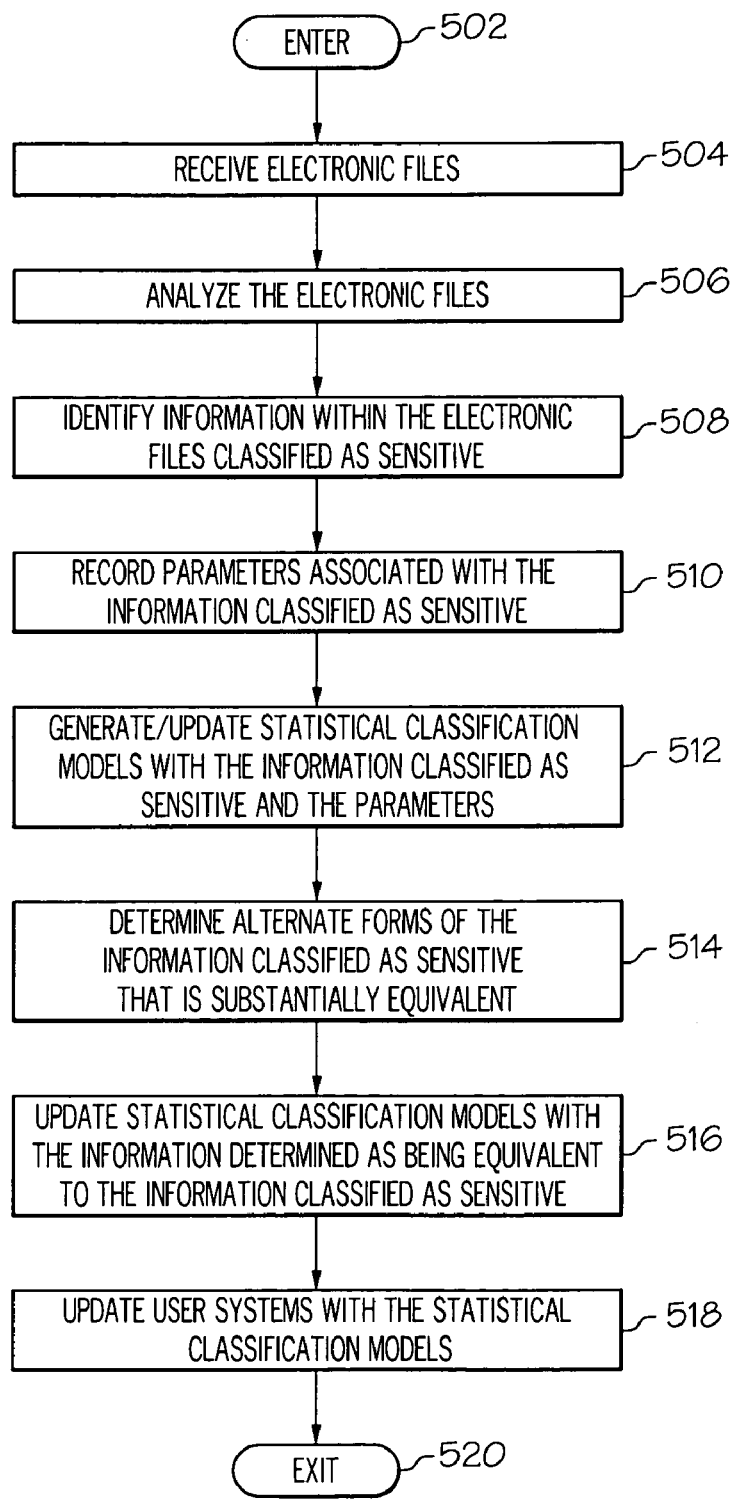
FIG. 5 is an operational flow diagram illustrating one process of generating/updating a statistical classification model according to one embodiment of the present invention.

FIG. 5 is an operational flow diagram illustrating one process of creating/updating a statistical classification model 132 according to one embodiment of the present invention. The operational flow of FIG. 5 begins at step 502 and flows directly to step 504. The information classifier 126, at step 504, receives electronic files 120 from a user, an administrator, and/or an automated agent. These electronic files 120 include electronic information as discussed above.

The information classifier 126, at step 506, analyzes the electronic files 120. Information within the electronic files 120 tagged as being sensitive, at step 508, is then identified by the information classifier 126. The information classifier 126, at step 510, records parameters and context information such as: is the sensitive information an entire sentence(s), paragraph(s), word(s), page(s), who the creator was, who the intended recipient was, and the like.

The information classifier 126, at step 512, generates and/or updates one or more statistical classification models 132 with the information identified as being sensitive and its associated parameters and context. The information classifier 126, at step 514, determines alternate forms of the sensitive information that are substantially equivalent to the sensitive information, as discussed above. The information classifier

126, at step 516, updates the statistical classification model(s) 132 to include this equivalent information. The information classifier 126, at step 518, updates the user systems 102,104 with the statistical classification models 132. The control flow then exits at step 520.

An Example of a Process for Identifying Sensitive Information

Figure 6:
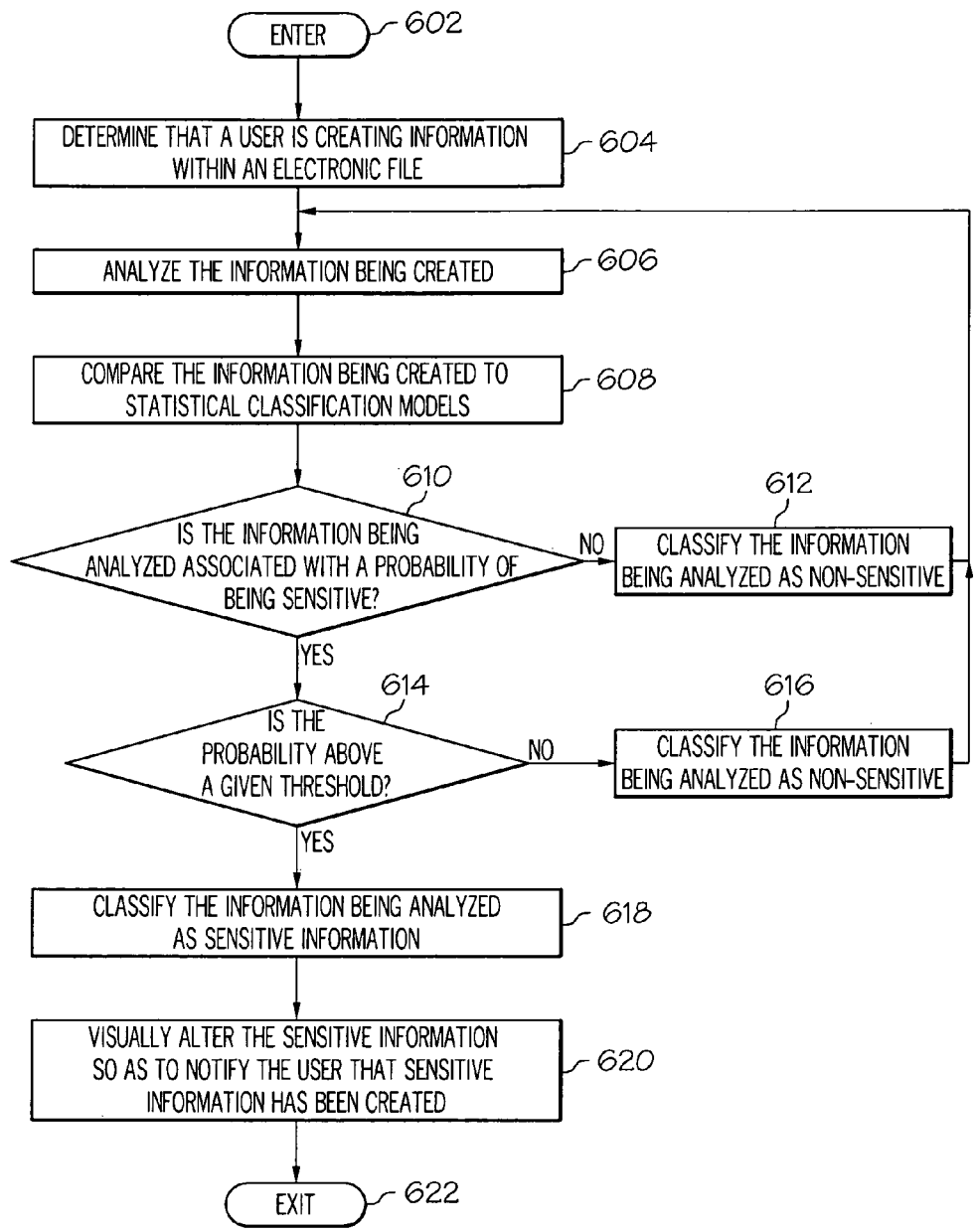
FIG. 6 is an operational flow diagram illustrating one process of identifying sensitive information within an electronic file according to one embodiment of the present invention.

FIG. 6 is an operational flow diagram illustrating one process of identifying sensitive information within an electronic file 120 according to one embodiment of the present invention. The operational flow of FIG. 6 begins at step 602 and flows directly to step 604. It should be noted that although the following discussion is with respect to the information manager 110 at the user system 102, this discussion is also applicable to the information classifier 126 as well.

The information manager 110, at step 604, determines that a user is creating information within an electronic file 120. The information manager 110, at step 606, analyzes the information being created. The information being created, at step 608, is compared to local statistical classification models 124 by the information manager 110. The information manager 110, at step 610, determines if the information being analyzed is associated with a probability of being sensitive. If the result of this determination is negative, the information manager 110, at step 612, classifies the information being analyzed as non-sensitive information. The control flow returns to step 606 where additional information is then analyzed.

If the result of this determination is positive, the information manager 110, at step 614 determines of the probability of being sensitive information associated with the information is above a given threshold. If the result of this determination is negative, the information manager 110, at step 616, classifies the information being analyzed as non-sensitive information. The control flow then returns to step 606 where additional information is then analyzed. If the result of this determination is positive, the information manager 110, at step 618, classifies the information as sensitive information. The information manager 110, at step 620, then visually alters the information classified as sensitive so as to notify the user that sensitive information has been created. The control flow then exits as step 622.

An Example of Preventing Access to Sensitive Information

Figure 7:
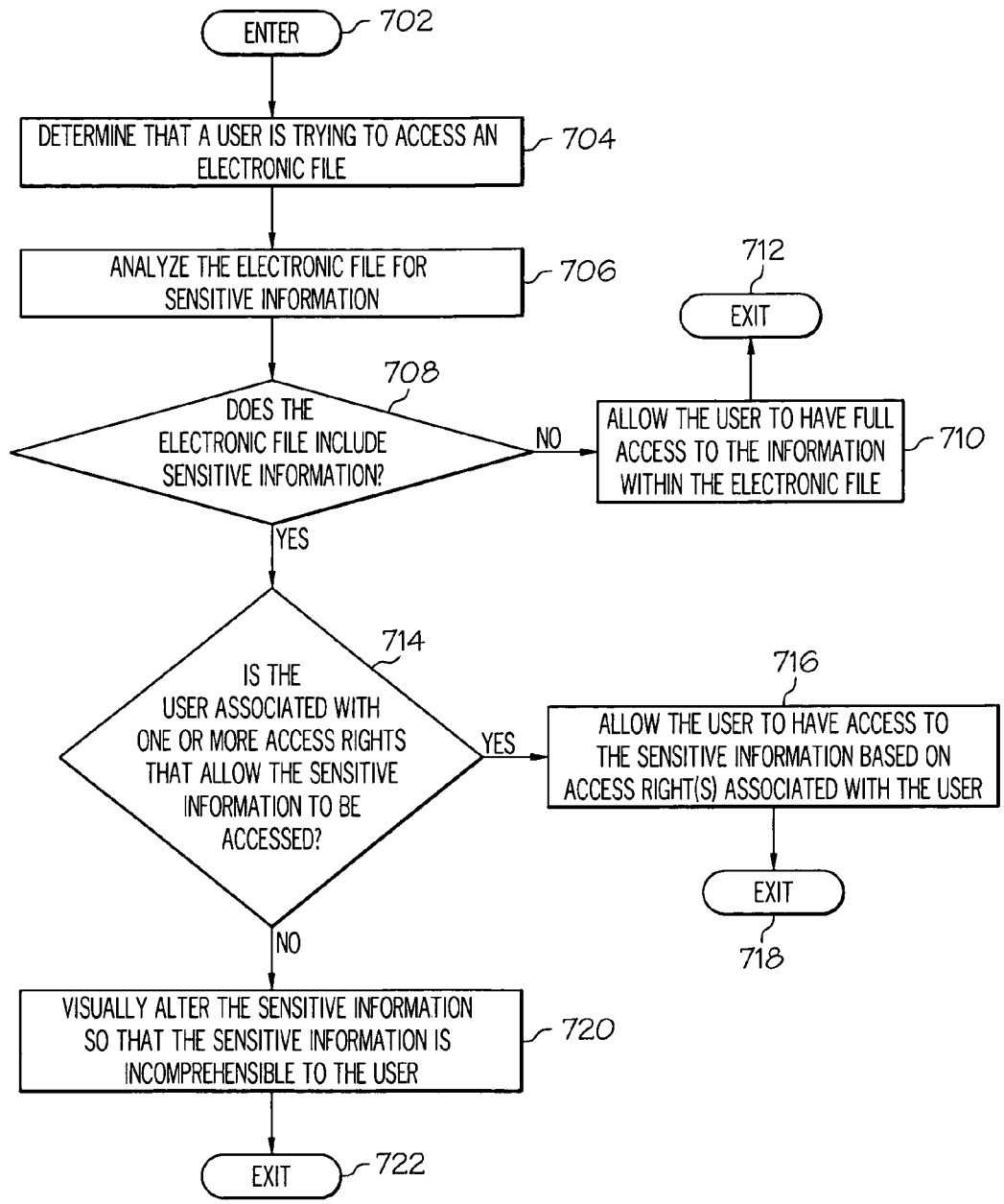
FIG. 7 is an operational flow diagram illustrating one process of preventing access to sensitive information within an electronic file according to one embodiment of the present invention.

FIG. 7 is an operational flow diagram illustrating one process of preventing access to sensitive information within an electronic file 120 according to one embodiment of the present invention. The operational flow of FIG. 7 begins at step 702 and flows directly to step 704. It should be noted that although the following discussion is with respect to the information manager 110 at the user system 102, this discussion is also applicable to the information classifier 126 as well.

The information manager 110, at step 704, determines that a user is trying to access an electronic file 120. The information manager 110, at step 706, analyzes the electronic file 120 for sensitive information. The information manager 110, at step 708, determines whether the electronic file 120 includes sensitive information. For example, the information manager 110 analyzes the file for metadata indicating that information is of a sensitive nature and/or compares the information to local statistical classification models 124 as discussed above.

If the result of this determination is negative, the information manager 110, at step 710, allows the user to have full access to the information within the electronic file 120. The control flow then exits at step 712. If the result of this determination is positive, the information manager 110, at step 714, determines if the user is associated with one or more access rights that allow the sensitive information to be accessed. If the result of this determination is positive, the information manager 110, at step 716, allows the user to access the sensitive information based on the access right(s) associated with the user. The control flow then exits at step 718. If the result of this determination is negative, the information manager 110, at step 720, visually alters the sensitive information so as to be incomprehensible to the user as discussed above. The control flow then exits at step 722.

Another Example of Identifying Sensitive Information

Figure 8:
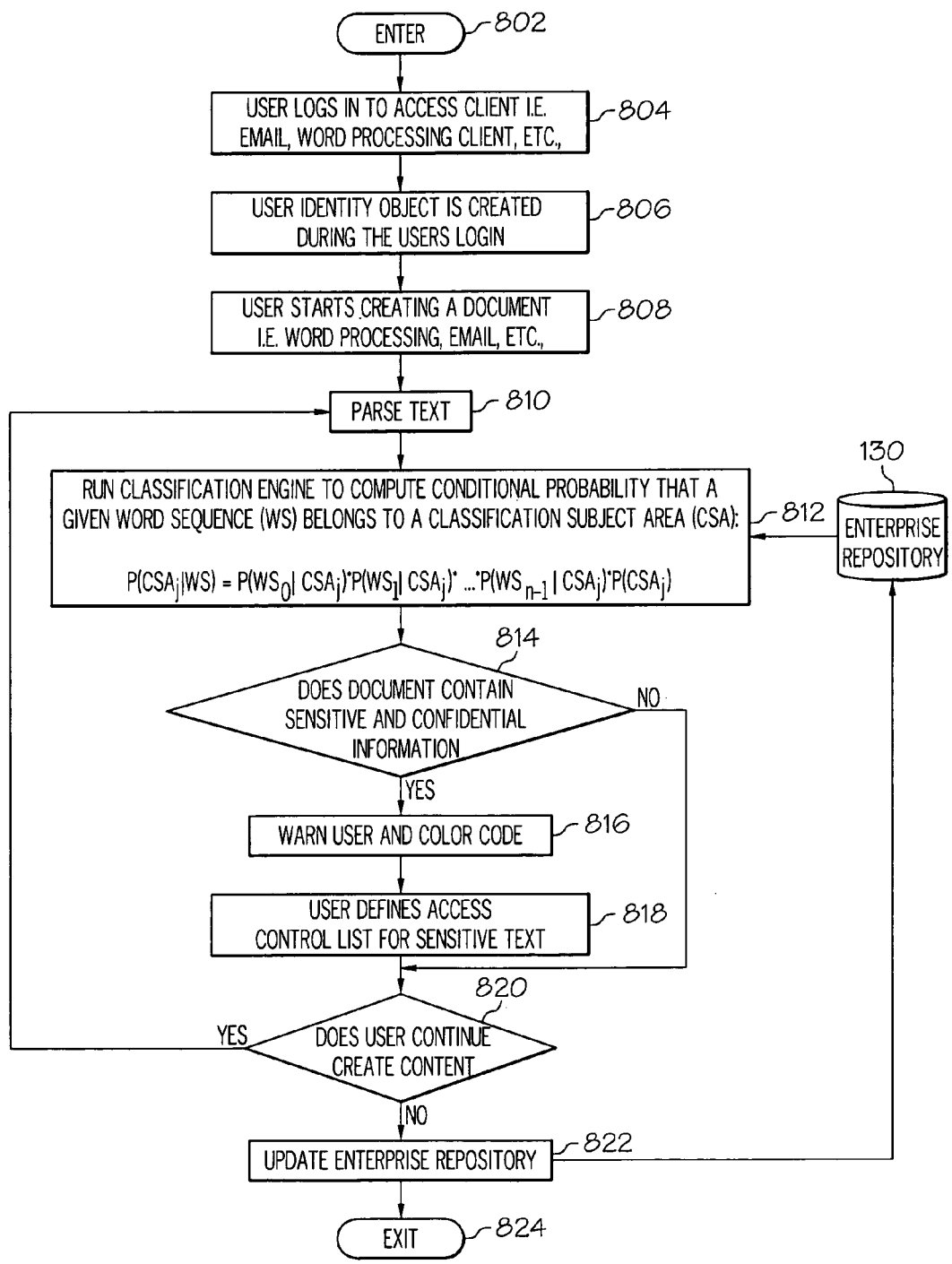
FIG. 8 is an operational flow diagram illustrating another process of identifying and classifying sensitive information.

FIG. 8 is an operational flow diagram illustrating another process of identifying and classifying sensitive information. The operational flow of FIG. 8 begins at step 802 and flows directly to step 804. A user, at step 804, logs in to access a client such as an email or word processing client. A user identity object, at step 806, is created during the login. The user, at step 808, starts creating a document such as an email or word processing file. The information classifier 126, at step 810, parses the text in the document created by the user.

The information classifier 126, at step 812, runs a classification engine to compute conditional probability that a given word sequence (WS) belongs to a classification subject area (CSA). The information classifier 126, at step 814, determines if the document includes sensitive and confidential information by utilizing information within the database 130. If the result of this determination is negative, the control flows to step 820. If the result of this determination is positive, the information classifier 126, at step 816, warns the user that the document includes sensitive and/or confidential information. The user, at step 818, then defines an access control list for the sensitive information.

The information classifier 126, at step 820, determines if the user is continuing to create content. If the result of this determination is positive, the control flow returns to step 810. If the result of this determination is negative, the information classifier 126, at step 822, updates the database 130 with the sensitive information detected and the access control information created by the user. The control flow then exits at step 824.

An Example of Training the Classification Engine

Figure 9:
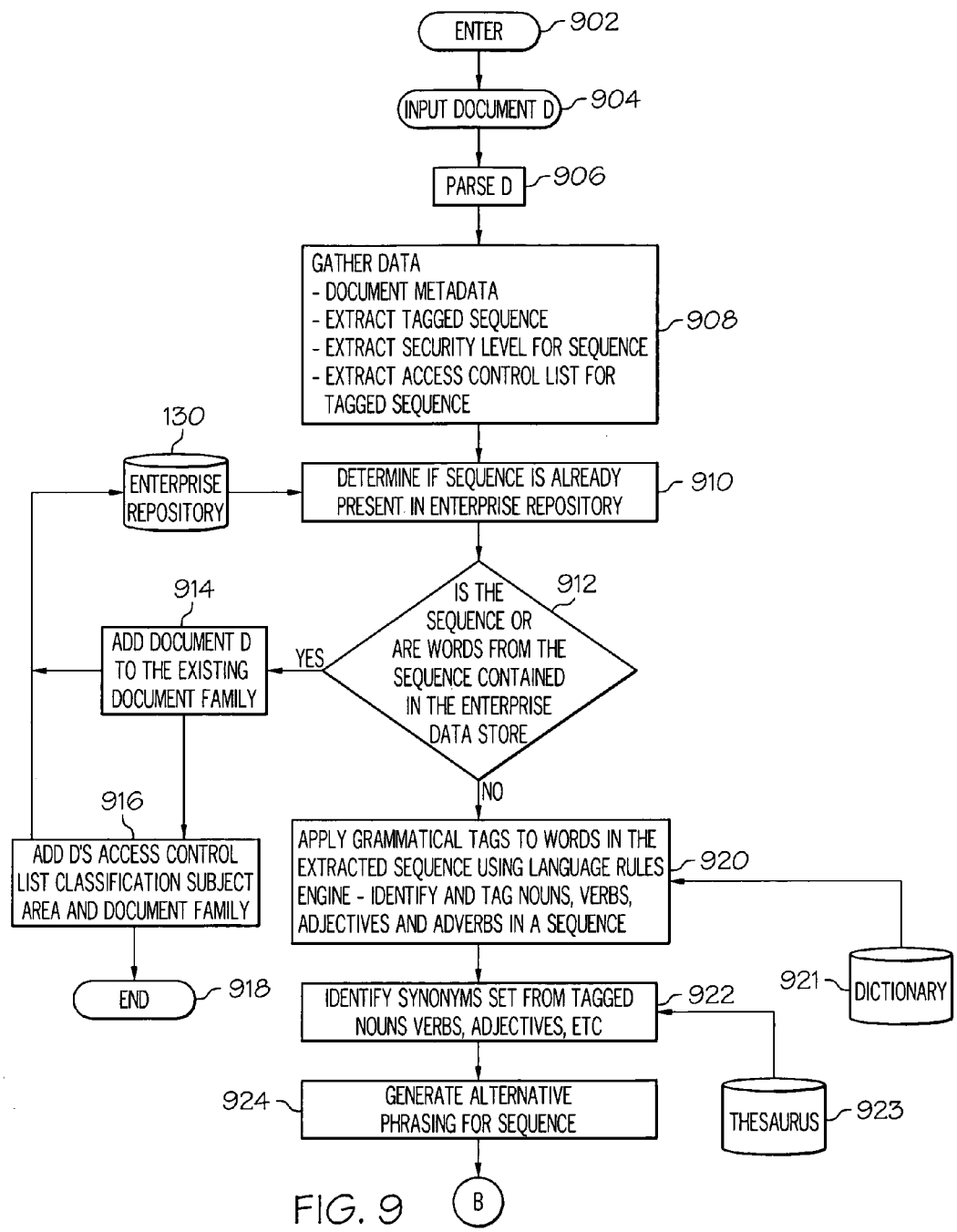
FIGS. 9-10 are operational flow diagrams illustrating one process of training an information classifier.
Figure 10:
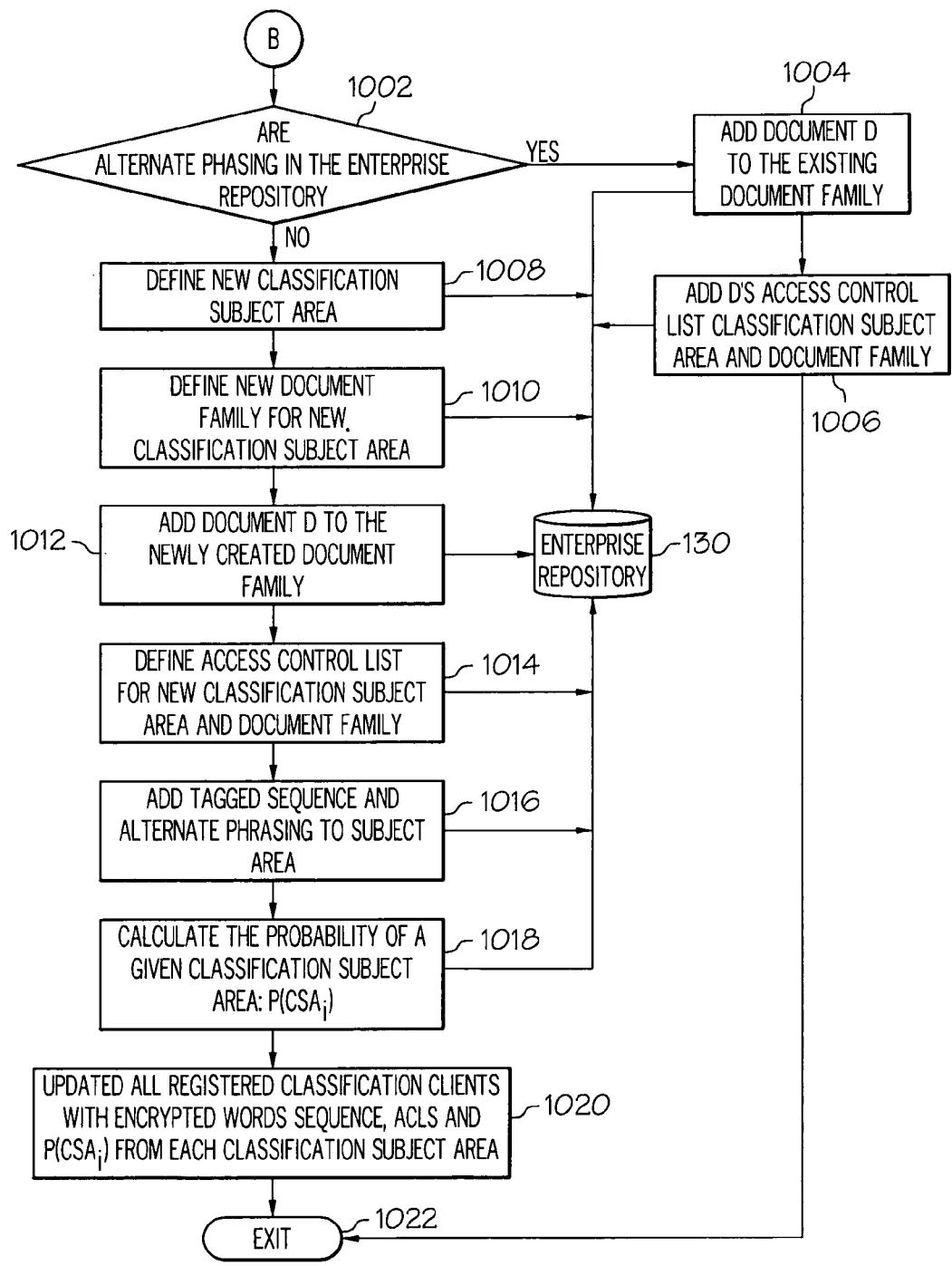

FIGS. 9-10 are operational flow diagrams illustrating one process of training the information classifier 126. The operational flow of FIG. 9 begins at step 902 and flows directly to step 904. The information classifier 126, at step 904, inputs document D and parses document D at step 906. The information classifier 126, at step 908, gathers data from the document D such as document metadata, tagged sequence information, security level information for sequence, access control list information for the tagged sequence.

The information classifier 126, at step 912, determines if the sequence or words from the sequence included in the database 130. If the result of this determination is positive, the information classifier 126, at step 914, adds document D to the existing document family. The information classifier 126, at step 916, add document D's access control classification subject area and document family to the database 130. The control flow then ends at step 918.

If the result of the determination at step 912 is negative, identifies grammatical tag words in the extracted sequence using language rules and a dictionary 921 at step 920. The information classifier 126 identifies and tags nouns, verbs, adjectives, and adverbs in a sequence. The information classifier 126, at step 922, identifies synonyms set from the tagged nouns, verbs, adjective, etc. using a thesaurus 923. The information classifier 126, at step 924 generates alternative phrasing for the extracted sequence. The control then flows to entry point B of FIG. 10.

The information classifier 126, at step 1002, determines if alternate phrasings exist in the database 130. The result of this determination is positive, the information classifier 126, at step 1004, adds document D to the existing document family. The information classifier 126, at step 1006, adds document D's access control list classification subject area and document family to the database 130. The control flow then exits at step 1022.

If the result of the determination at step 1002 is negative, the information classifier 126, at step 1008, defines a new classification subject area. The information classifier 126, at step 1010, defines a new document family for the new classification subject area. The information classifier 126, at step 1012, adds document D to the newly created document family, at step 1014, defines access control list for new classification subject area, and document family, and adds tagged sequence and alternate phrasing to the subject area, at step 1016. The information classifier 126, at step 1018, calculates the probability of a given classification subject area: $P(CSA_i)$. The information classifier 126, at step 1020, updates all registered classification clients with encrypted words sequence, ACLS, and $P(CSA_i)$ from each classification subject area. The control flow then exits at step 1022.

Non-Limiting Examples

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A method for managing information within an electronic file, the method comprising:

analyzing a plurality of information sets within an electronic file;

comparing at least one of the information sets in the plurality of information sets to at least one statistical classification model, wherein the statistical classification model includes one or more probabilities associated with a plurality of analyzed information sets, wherein the one or more probabilities indicate a first likelihood that a respective analyzed information set is classified as sensitive information and a second likelihood that the respective analyzed information set is classified as non-sensitive information;

continually adaptively updating the at least one statistical classification model that includes the one or more probabilities associated with the plurality of analyzed information sets, adapting the one or more probabilities associated with the plurality of analyzed information sets based on continually received information;

determining that the at least one information set substantially matches at least one analyzed information set in the statistical classification model;

determining that a probability associated with the at least one analyzed information set is above a given threshold;

classifying, in response to determining that the probability associated with the at least one analyzed information set is above a given threshold, the at least one information set as sensitive information;

in response to classifying the at least one analyzed information set classified as sensitive information, identifying, without user intervention, at least one equivalent form of the at least one analyzed information set;

updating the at least one statistical classification model with the at least one equivalent form that has been identified;

in response to the at least one analyzed information set being classified as sensitive information, record a context of the at least one analyzed information set, wherein the context indicates that the at least one analyzed information set is one of a sentence, a paragraph, a word, and an entire page; and update the at least one statistical classification model with the context that has been recorded for the at least one analyzed information set that has been classified as sensitive information.

2. The method of claim 1, further comprising:

determining that the at least one information set fails to substantially match at least one analyzed information set in the statistical classification model; and classifying, in response to determining that the at least one information set fails to substantially match at least one analyzed information set in the statistical classification model, the at least one information set as non-sensitive information.

3. The method of claim 1, further comprising:

determining that the probability associated with the at least one analyzed information set is below a given threshold; and classifying, in response to determining that the probability associated with the at least one analyzed information set is below a given threshold, the at least one information set as non-sensitive information.

4. The method of claim 1, further comprising:

determining that a user is currently creating the information classified as sensitive information in the electronic file; and visually altering the information that has been classified as sensitive information, wherein the visually altering notifies the user that sensitive information has been created, and wherein the visually altering is performed as the user is currently creating the information classified as sensitive information.

5. The method of claim 1, further comprising:

determining that a user is requesting access to the electronic file;

determining that the electronic file includes the information classified as sensitive information; and visually altering the information that has been classified as sensitive information, wherein the visually altering makes the information classified as sensitive incomprehensible to the user.

6. The method of claim 1, further comprising:

determining that a user is requesting access to the electronic file;

determining that the electronic file includes the information classified as sensitive information;

determining if the user is associated with an access right that allows access to the sensitive information;

preventing the user from accessing at least the sensitive information in response to determining that the user fails to be associated with an access right that allows access to the sensitive information; and granting the user access to the sensitive information based on the access right in response to determining that the user is associated with an access right that allows access to the sensitive information.

7. The method of claim 6, wherein preventing the user from accessing at least the sensitive information, further comprises:

visually altering the information that has been classified as sensitive information, wherein the visually altering makes the information classified as sensitive incomprehensible to the user.

8. The method of claim 1, further comprising:
generating the at least one statistical classification model, wherein the generating comprises:
receiving a plurality of electronic files each comprising at least one information set designated as sensitive information;
determining a set of parameters and a set of contexts associated with the at least one information set for each of the plurality of electronic files; and
storing each of the at least one information sets, the set of parameters, and the set of contexts in the at least one statistical classification model.

9. The method of claim 8, wherein the generating comprises:
determining at least one equivalent information set for each of the at least one information sets that substantially matches the respective at least one information set; and
storing at least one equivalent information set for each of the at least one information sets in the at least one statistical classification model.

10. The method of claim 8, wherein the determining a set of parameters and a set of contexts associated with the at least one information set for each of the plurality of electronic files, further comprises:
analyzing each of the least one information sets at least one of:
a page level;
a paragraph level;
a sentence level;
a word level; and
a field level.

11. The method of claim 1, wherein the at least one statistical classification model is stored and continually adaptively updated at one or more of an information classification server and a user system, and further comprising at least one of:
receiving, at a user system, an updated at least one statistical classification model transmitted from the information classification server, and storing the received updated at least one statistical classification model at the user system; and
transmitting, at a user system, an updated at least one statistical classification model to the information classification server.

12. An information processing system for managing information within an electronic file, the information processing system comprising:
a memory;
a processor communicatively coupled to the memory; and
an information manager communicatively coupled to the memory and the processor, wherein the information manager is configured to:
analyze a plurality of information sets within an electronic file;
compare at least one of the information sets in the plurality of information sets to at least one statistical classification model, wherein the statistical classification model includes one or more probabilities associated with a plurality of analyzed information sets, wherein the one or more probabilities indicate a first likelihood that a respective analyzed information set is classified as sensitive information and a second likelihood that the respective analyzed information set is classified as non-sensitive information,
continually adaptively update the at least one statistical classification model that includes the one or more probabilities associated with the plurality of analyzed information sets, adapting the one or more probabilities associated with the plurality of analyzed information sets based on continually received information;
determine that the at least one information set substantially matches at least one analyzed information set in the statistical classification model;
determine that a probability associated with the at least one analyzed information set is above a given threshold;
classify, in response the probability associated with the at least one analyzed information set being above a given threshold, the at least one information set as sensitive information;
in response to the at least one analyzed information set being classified as sensitive information, identify, without user intervention, at least one equivalent form of the at least one analyzed information set;
update the at least one statistical classification model with the at least one equivalent form that has been identified;
in response to the at least one analyzed information set being classified as sensitive information, record a context of the at least one analyzed information set, wherein the context indicates that the at least one analyzed information set is one of a sentence, a paragraph, a word, and an entire page; and
update the at least one statistical classification model with the context that has been recorded for the at least one analyzed information set that has been classified as sensitive information.

13. The information processing system of claim 12, wherein the information manager is further adapted to:
determine that the at least one information set fails to substantially match at least one analyzed information set in the statistical classification model; and
classify, in response to the at least one information set failing to substantially match at least one analyzed information set in the statistical classification model, the at least one information set as non-sensitive information.

14. The information processing system of claim 12, wherein the information manager is further adapted to:
determine that the probability associated with the at least one analyzed information set is below a given threshold; and
classify, in response to the probability associated with the at least one analyzed information set being below a given threshold, the at least one information set as non-sensitive information.

15. The information processing system of claim 12, wherein the information manager is further adapted to:
determine that a user is requesting access to the electronic file;
determine that the electronic file includes the information classified as sensitive information;
visually alter the information that has been classified as sensitive information, wherein the visually altering makes the information classified as sensitive incomprehensible to the user.

16. A computer program storage product for managing information within an electronic file, the computer program storage product comprising instructions for:
analyzing a plurality of information sets within an electronic file;
comparing at least one of the information sets in the plurality of information sets to at least one statistical classification model, wherein the statistical classification model includes one or more probabilities associated with a plurality of analyzed information sets, wherein the one or more probabilities indicate a first likelihood that a respective analyzed information set is classified as sensitive information and a second likelihood that the respective analyzed information set is classified as non-sensitive information, wherein the first and second likelihoods are based at least on other information sets within a given context of the respective analyzed information set;

continually adaptively updating the at least one statistical classification model that includes the one or more probabilities associated with the plurality of analyzed information sets, adapting the one or more probabilities associated with the plurality of analyzed information sets based on continually received information;

determining that the at least one information set substantially matches at least one analyzed information set in the statistical classification model;

determining that a probability associated with the at least one analyzed information set is above a given threshold;

classifying, in response to determining that the probability associated with the at least one analyzed information set is above a given threshold, the at least one information set as sensitive information;

in response to classifying the at least one analyzed information set classified as sensitive information, identifying, without user intervention, at least one equivalent form of the at least one analyzed information set;

updating the at least one statistical classification model with the at least one equivalent form that has been identified;

in response to the at least one analyzed information set being classified as sensitive information, record a context of the at least one analyzed information set, wherein the context indicates that the at least one analyzed information set is one of a sentence, a paragraph, a word, and an entire page; and update the at least one statistical classification model with the context that has been recorded for the at least one analyzed information set that has been classified as sensitive information.

17. The computer program storage product of claim 16, further comprising instructions for:

determining if the at least one information set fails to substantially match at least one analyzed information set in the statistical classification model; and classifying, in response to determining that the at least one information set fails to substantially match at least one analyzed information set in the statistical classification model, the at least one information set as non-sensitive information;

determining if the probability associated with the at least one analyzed information set is below a given threshold; and classifying, in response to determining that the probability associated with the at least one analyzed information set is below a given threshold, the at least one information set as non-sensitive information.

18. The computer program storage product of claim 16, further comprising instructions for:

determining if a user is currently creating the information classified as sensitive information in the electronic file;

visually altering the information that has been classified as sensitive information in response to determining that the user is currently creating the information classified as sensitive information, wherein the visually altering notifies the user that sensitive information has been created;

determining if a user is requesting access to the electronic file;

determining, in response to the user requesting access to the electronic file, that the electronic file includes the information classified as sensitive information; and visually altering the information that has been classified as sensitive information in response to determining that the electronic file includes the information classified as sensitive information, wherein the visually altering makes the information classified as sensitive incomprehensible to the user.

19. The computer program storage product of claim 16, further comprising instructions for:

determining that a user is requesting access to the electronic file;

determining that the electronic file includes the information classified as sensitive information in the electronic file;

determining if the user is associated with an access right that allows access to the sensitive information;

preventing the user from accessing at least the sensitive information in response to determining that the user fails to be associated with an access right that allows access to the sensitive information; and granting the user access to the sensitive information based on the access right in response to determining that the user is associated with an access right that allows access to the sensitive information.

20. The computer program storage product of claim 16, wherein the at least one statistical classification model is stored and continually adaptively updated at one or more of an information classification server and a user system, and the computer program storage product further comprising instructions for at least one of:

receiving, at a user system, an updated at least one statistical classification model transmitted from the information classification server, and storing the received updated at least one statistical classification model at the user system; and transmitting, at a user system, an updated at least one statistical classification model to the information classification server.

* * * * *